United States Patent [19]
Stevenson et al.

[11] Patent Number: 6,133,453
[45] Date of Patent: *Oct. 17, 2000

[54] METHOD FOR MAKING SUBSTITUTED INDOLES

[75] Inventors: Robert Stevenson; Milind P. Sant, both of Lexington; Reem Haider, Woburn; Ahmed Hilmy, Malden; Emile Al-Farhan, Dedham, all of Mass.

[73] Assignee: Pharm-Eco Laboratories, Inc., Lexington, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 09/309,329

[22] Filed: May 11, 1999

Related U.S. Application Data

[60] Provisional application No. 60/085,639, May 15, 1998.

[51] Int. Cl.⁷ ..................... C07D 209/20; C07D 209/04; C07D 209/02
[52] U.S. Cl. ........................ 548/496; 548/508; 548/468
[58] Field of Search .................. 548/484, 489, 548/491, 490, 496, 508, 468

[56] References Cited

U.S. PATENT DOCUMENTS

| | | |
|---|---|---|
| 4,600,723 | 7/1986 | Short et al. . |
| 4,665,086 | 5/1987 | Short et al. . |
| 4,855,305 | 8/1989 | Cohen . |
| 4,945,103 | 7/1990 | Cohen . |
| 5,093,352 | 3/1992 | Dubocovich . |
| 5,103,020 | 4/1992 | Albinson et al. ................ 548/504 |
| 5,175,308 | 12/1992 | Honda et al. .................... 548/508 |
| 5,179,211 | 1/1993 | Blank et al. ..................... 548/508 |
| 5,242,941 | 9/1993 | Lewy et al. . |
| 5,272,141 | 12/1993 | Fraschini et al. . |
| 5,403,851 | 4/1995 | D'Orlando et al. . |
| 5,580,878 | 12/1996 | D'Orlando et al. . |
| 5,932,743 | 8/1999 | Collini et al. ..................... 548/508 |
| 5,986,106 | 11/1999 | Khau et al. ....................... 548/493 |

FOREIGN PATENT DOCUMENTS

| | | |
|---|---|---|
| 0 500 086 A1 | 8/1992 | European Pat. Off. . |
| 0 675 109 A1 | 10/1995 | European Pat. Off. . |
| 2 499 987 | 8/1982 | France . |

OTHER PUBLICATIONS

Waldhauser, F., et al., "Sleep labortory investigations on hypnotic properties of melatonin," *Psychopharmacology,* 100:222–226 (1990).

Vollrath, et al., *Bioscience,* 29:327 (1981).

Dollins, A.B., et al., "Effect of inducing nocturnal serum melatonin concentrations in daytime on sleep, mood, body temperature, and performance," *Proc. Natl. Acad. Sci.,* 91:1824–1828 (1994).

Sack, R.L., et al., "Human Melatonin Production Decreases with Age,"*Pineal Res.,* 3:379–388 (1986).

Fort, P., et al., "Neonatal Thyroid Disease: Differential Expression in Three Successive Offspring," *J. Clin. Metab.,* 66(3):645–647 (1988).

Van Coeverden, A., et al., "Neuroendocrine rhythms and sleep in aging men," *Am. J. Physiolog.,* 260:E651–E661 (1991).

Sugden, D., "Psychopharmacological Effects of Melatonin in Mouse and Rat," *J. Pharmacol. Exp. Ther.,* 227(3):587–591 (1983).

Brailowsky, S., "Effects of Melatonin on the Photosensitive Epilepsy of the Baboon, *Papio Papio,*" *Electroencephalo. Clin. Neurophysiol.,* 41:314–319 (1976).

Golombek, D.A., et al., "Time–dependent anticonvulsant activity of melatonin in hamsters," *Eur. J. Pharmacol.,* 210:253–258 (1992).

Miles, A. and Philbrick, D.R.S., "Melatonin and Psychiatry," *Biol. Psychiatry,* 23:405–425 (1988).

Sandyk, R. and Kay, S.R., "Pineal Melatonin in Schizophrenia: A Review and Hypothesis," *Schizophr. Bull.,* 16(4):653–662 (1990).

McIntyre, I.M., et al., "Plasma Concentrations of Melatonin in Panic Disorder," *Am. J. Psychiat.,* 147(4):462–464 (1990).

(List continued on next page.)

*Primary Examiner*—Deborah C. Lambkin
*Attorney, Agent, or Firm*—Hamilton, Brook, Smith & Reynolds, P.C.

[57] ABSTRACT

Disclosed is a method of preparing a compound represented by the following structural formula:

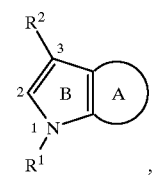

and physiological salts thereof.

$R^1$ is —H, an aliphatic group, a substituted aliphatic group, an aryl group or a substituted aryl group.

$R^2$ is a substituted or unsubstituted 2-hydroxy-1-ethyl group.

Ring A is a substituted or unsubstituted aryl group.

Ring B is substituted or unsubstituted at position two.

The method comprises reacting a substituted or unsubstituted aryl hydrazine or salt derived from a substituted or unsubstituted aryl hydrazine with a compound represented by the following structural formula:

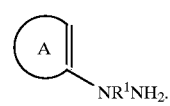

12 Claims, 2 Drawing Sheets

OTHER PUBLICATIONS

Fevre, M., et al., "LH and Melatonin Secretion Patterns in Pubertal Boys," *J. Clin. Endocrinol. Metab.*, 47(6):1383–1386 (1978).

Parry, B.L., et al., "Treatment of a Patient with Seasonal Premenstrual Syndrome," *Am. J. Psychiatry*, 144(6):762–766 (1987).

Waldhauser, F., et al., "Serum Melatonin in Central Precocious Puberty is Lower than in Age–Matched Prepubertal Children," *J. Clin. Endocrinal. Metab.*, 73(4):793–796 (1991).

Bispink, G., et al., "Influence of Melatonin on the Sleep–Independent Component of Prolactin Secretion," *J. Pineal Res.*, 8:97–106 (1990).

Cagnacci, A., et al., "Amplification of Pulsatile LH Secretion by Exogenous Melatonin in Women," *J. Clin. Endocrinol. Metab.*, 73 (1):210–212 (1991).

Voordow, B.C.G., et al., "Melatonin and Melatonin–Progestic Combinations Alter Pituitary–Ovvarian Function in Women and Can Inhibit Ovulation," *J. Clin. Endocrinol. Metab.*, 74(1):108–117 (1992).

Grandberg, I.I., et al., "Indoles. XXXII. Synthesis of tryptophols," Chemical Abstracts, 78(7):465 (Feb. 19, 1973). Abstract.

METHOD FOR MAKING SUBSTITUTED INDOLES

RELATED APPLICATION

This application claims the benefit of U.S. Provisional Application No. 60/085,639, filed on May 15, 1998, entitled "Practical Method for Making Substituted Indoles," the entire teachings of which are incorporated herein by reference.

BACKGROUND OF THE INVENTION

Melatonin (Structural Formula I) is a hormone that is synthesized in the pineal gland and in the eye and is involved in the regulation of circadian and circannual rhythms.

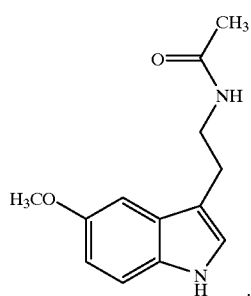

Levels of melatonin are high at night because exposure to light inhibits its synthesis. In addition, melatonin has been shown to lower the body temperature and to have a sedative effect.

Melatonin, and compounds structurally related to melatonin (e.g., substituted indoles), are useful in treating a number of human disorders. For example, sleep disorders, particularly in the elderly, have been shown to respond to treatment with melatonin (Waldhauser, et al, *Psychopharmacology*, (1990), 100:222; Vollrath, et al *Bioscience*, (1981), 29:327; Dollins, et al, *Proc. Natl. Acad. Sci.*, (1994), 99:1824). In addition, melatonin has been useful in treating chronobiologic conditions, such as jet lag or work shift changes (Short, et al, U.S. Pat. Nos. 4,600,723 and 4,665,086; Lewy, et al, U.S. Patent No. 5,242,941).

Neurodegenerative diseases, such as Parkinson's disease and Alzheimer's disease, may also benefit from treatment with melatonin or melatonin derivatives, since levels of melatonin decrease with age (Sack, et al, *Pineal Res.*, (1986), 4:379; Waldhauser, et al, *J. Clin. Metab.*, (1988), 66:645; Van Coevorden, et al, *Am. J. Physiolog.*, (1991), 260:E651). Patients with Alzheimer's disease in particular exhibit circadian rhythm disruptions, and therefore, may benefit from these compounds (Kandel, et al, *Principles of Neuroscience*, 3rd Edition (1991), Appleton & Lange, Norwalk, Conn., p. 808).

Melatonin has also been shown to have analgesic (Sugden, *J. Pharmacol. Exp. Ther.*, (1983), 227:587) and antiseizure activity (Brailowsky, *Electroencephalo. Clin. Neurophysiol.*, (1976), 41:314; Golombek, et al, *Eur. J. Pharmacol.*, (1992), 210:253). Therefore, compounds related to melatonin may be effective in treating conditions such as migraine headache and epilepsy.

Psychiatric disorders, such as seasonal affective disorder, anxiety disorders, depression, schizophrenia, and mania, may respond to treatment with melatonin related compounds (Dubocovich, U.S. Pat. No. 5,093,352; Miles, et al, *Biol. Psychiatry*, (1988), 23:405; Sandyk, et al, *Schizophr. Bull.*, (1990), 16:653). For example, manic or depressed patients often exhibit sleep disorders. In addition, melatonin secretion has been shown to be abnormal in humans suffering from anxiety disorder (Mcintyre, et al., *Am. J. Psychiat.*, (1990), 147:462).

Compounds related to melatonin may also be useful in treating precocious puberty, premenstrual syndrome or as fertility or contraceptive agents because production of melatonin is known to change at puberty. In addition, in seasonal breeding species melatonin regulates fertility, hibernation and puberty (Fevre, et al., *J. Clin. Endocrinol. Metab.*, (1978), 47:1383; Parrey, et al., *Am. J. Psychiatry*, (1987), 144:762; Waldhauser, et al., *J. Clin. Endocrinol. Metab.*, (1991), 73:793; Bispink, et al., *J. Pineal Res.*, (1990), 8:97; Cagnacci, et al., *J. Clin. Endocrinol. Metab.*, (1991), 73:210; Voordouw, et al., *J. Clin. Endocrinol. Metab.*, (1992), 73:107; Fraschini, et al., 5,272,141; Cohen, et al., U.S. Pat. Nos. 4,855,305 and 4,945,103). Therefore, compounds related to melatonin may have applications to animal husbandry.

As described above, abnormalities in melatonin production have been implicated in a number of human and animal disorders. Compounds which are structurally related to melatonin are expected to have many therapeutic applications because they have the potential to mimic the activity of melatonin or block melatonin receptors. A versatile synthetic route that would allow for a variety of substitution patterns would facilitate the production of melatonin related compounds. Melatonin related compounds and their uses are more fully described in U.S. Pat. Nos. 5,403,851 and 5,580,878, the entire teachings of which are hereby incorporated by reference.

SUMMARY OF THE INVENTION

Disclosed herein is a method of preparing substituted, fused polycyclic nitrogen-containing heteroaromatic compounds, including substituted indoles and physiologically acceptable salts thereof. The substituted, fused polycyclic nitrogen-containing heteroaromatic compound is represented by Structural Formula (II):

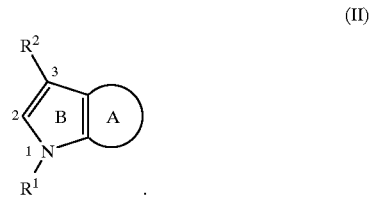

$R^1$ is —H, an aliphatic group, a substituted aliphatic group, an aryl group or a substituted aryl group. For example, $R^1$ is —H or a C1–C5 alkyl group.

$R^2$ is a substituted or unsubstituted 2-hydroxy-1-ethyl group.

Ring A is a substituted or unsubstituted aryl group.

Ring B is substituted or unsubstituted at position two. A numbering system for the ring atoms of Ring B is provided in Structural Formula (II).

The method comprises the step of reacting a 2,3-dihydrofuran with a substituted or unsubstituted aryl hydrazine represented by Structural Formula (III) or with a salt derived from a compound having a formula represented by Structural Formula (III):

(III)

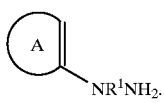

$R^1$ and ring A are as described above for Structural Formula (II).

In another embodiment, the fused polycyclic nitrogen-containing heteroaromatic compound is represented by structural formula (IV):

(IV)

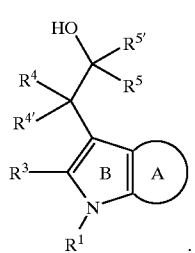

$R^1$ and ring A are as described for Structural Formula (II).

$R^3$, $R^4$, $R^{4'}$, $R^5$, and $R^{5'}$ are each, independently, —H, aliphatic groups, substituted aliphatic groups, aryl group, substituted aryl groups, halogens, halogenated aliphatic groups, nitro, nitrile, —C(O)NHR, —C(O)NRR, —NHC(O)R, —NRC(O)R, —OR, —SR, —S(O)R, —S(O)$_2$R.

R is an aliphatic group, a substituted aliphatic group, an aryl group or a substituted aryl group.

The method of preparing a compound represented by Structural Formula (IV) comprises the step of reacting a substituted or unsubstituted aryl hydrazine represented by Structural Formula (III) or a salt derived from a substituted or unsubstituted aryl hydrazine represented by Structural Formula (III) with a compound represented by Structural Formula (V):

(V)

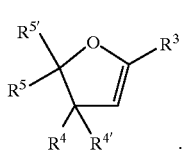

$R^3$, $R^4$, $R^{4'}$, $R^5$, and $R^{5'}$ are as described for Structural Formula (IV).

The method described above for preparing substituted, fused polycyclic nitrogen-containing heteroaromatic compounds provides access to a variety of compounds that are structurally related to melatonin, and therefore, facilitates the development of drugs for the treatment of conditions related to abnormalities in melatonin production.

DETAILED DESCRIPTION OF THE INVENTION

The features and other details of the method on the invention will now be more particularly described and pointed out in the claims. It will be understood that the particular embodiments of the invention are shown by way of illustration and not as limitations of the invention. The principle features of this invention can be employed in various embodiments without departing from the scope of the invention. All parts and percentages are by weight unless otherwise specified.

The method of preparing substituted, fused, polycyclic nitrogen-containing aromatic compounds represented by Structural Formula (II) comprises the step of reacting substituted or unsubstituted 2,3-dihydrofuran with a substituted or unsubstituted aryl hydrazine represented by Structural Formula (III) or a salt derived from a substituted or unsubstituted aryl hydrazine represented by Structural Formula (III).

In another embodiment, a method of preparing a fused polycyclic nitrogen-containing heteroaromatic compound represented by Structural Formula (IV) is disclosed. The method comprises the step of reacting a substituted or unsubstituted aryl hydrazine represented by Structural Formula (III) or a salt derived from a substituted or unsubstituted aryl hydrazine represented by Structural Formula (III) with a compound represented by Structural Formula (V).

Figure 1:
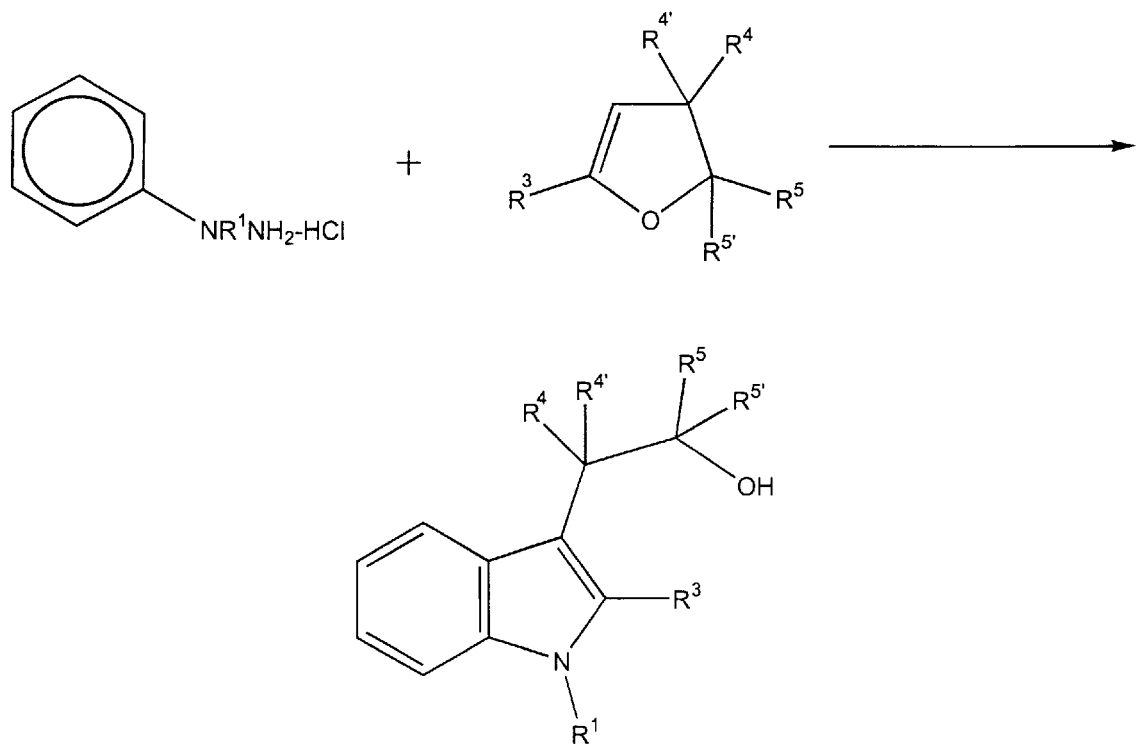
FIG. 1 is a reaction scheme showing the reaction of phenylhydrazine hydrochloride with a 2,3-dihydrofuran substituted at positions two, four or five with $R^3$, $R^4$, $R^{4'}$, $R^5$, and $R^{5'}$.

The 2,3-dihydrofuran is unsubstituted or substituted. As used herein, a substituted 2,3-dihydrofuran is a 2,3-dihydrofuran substituted at position two, four and/or five with one or more substitutents. For example, the reaction of phenylhydrazine hydrochloride with a 2,3-dihydrofuran substituted at positions two, four or five with $R^3$, $R^4$, $R^{4'}$, $R^5$ and $R^{5'}$ is shown schematically in FIG. 1.

In a preferred embodiment, the aryl hydrazine represented by Structural Formula (III) or derived salt is reacted with an unsubstituted 2,3-dihydrofuran. The fused polycyclic nitrogen-containing heteroaromatic compound formed by this reaction is represented by Structural Formula (VI):

(VI)

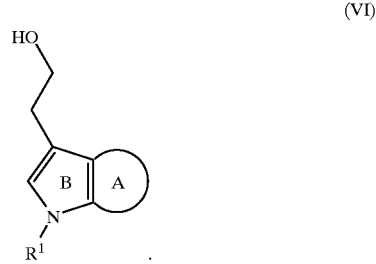

Ring A and $R^1$ are as described above for Structural Formula (II).

In another preferred embodiment, a substituted or unsubstituted 2,3-dihydrofuran is reacted with a phenyl hydrazine represented by Structural Formula (VII) or with a salt derived from a compound represented by Structural formula (VII):

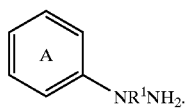

(VII)

The fused polycyclic nitrogen-containing heteroaromatic compound formed by this reaction is a substituted indole represented by Structural Formula (VIII):

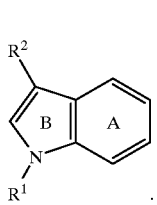

(VIII)

In Structural Formulas (VII) and (VIII), ring A is substituted or unsubstituted, ring B is substituted or unsubstituted at position 2, and $R^1$ and $R^2$ are as described for Structural Formula (II).

In a more specific embodiment, an unsubstituted 2,3-dihydrofuran is reacted with a phenyl hydrazine represented by Structural Formula (VII) or with a salt derived from a compound represented by Structural Formula (VII). The substituted indole formed by this reaction is represented by Structural Formula (IX):

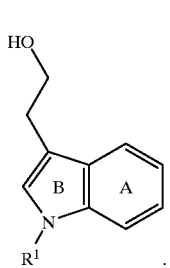

(IX)

In Structural Formula (IX), rings A is substituted or unsubstituted, and $R^1$ is as described for Structural Formula (II). In a preferred embodiment, $R^1$ is —H or —$CH_3$.

The reaction is generally carried out in an ethereal solvent which is miscible in water, for example, tetrahydrofuran (THF), glyme, diglyme or 1,4-dioxane. THF is a preferred solvent. A sufficient amount of water or other polar solvent is added to dissolve the hydrazine salt. Suitable polar solvents include alcohols (e.g., methanol, ethanol and isopropanol), nitroalkanes, acetonitrile, dimethyl sulfoxide, dimethylformamide and hexamethylphosphoramide.

The 2,3-dihydrofuran and the aryl hydrazine or aryl hydrazine salt are present generally in about equimolar amounts. However, one reagent can be present in a large excess relative to the other, for example, a two to three fold excess relative to the other. Preferably, the 2,3-dihydrofuran is present in a molar excess relative to the hydrazine salt up to about 50%, more preferably about 10%.

The 2,3-dihydrofuran and aryl hydrazine or aryl hydrazine salt are present at concentrations ranging from 0.25 M to about 5.0 M, preferably from about 0.25 M to about 0.75 M. The reagents can be mixed in any order. However, the 2,3-dihydrofuran is generally added to a mixture of the aryl hydrazine or aryl hydrazine salt in water and an ethereal solvent. Because the reaction is exothermic, the reagents are typically mixed slowly, e.g., dropwise. The optimal reaction time and temperature depends on factors such as the solvent and concentration, which the skilled artisan will be able to adjust so as to maximize the yield of product. Generally, after mixing, the reaction is maintained at temperatures ranging from room temperature to reflux until completion. Reaction completion can be monitored by usual methods, for example, by gas chromatography or thin layer chromatography.

The substituted, fused, polycyclic nitrogen-containing aromatic compounds represented by Structural Formulas (II), (IV), (VI), (VIII), and (IX) are obtained as the free base which can be converted to a salt by recrystallization with an acid such as succinic acid. Physiologically acceptable salts are preferred. The salt can be converted back to the free base by treating with a basic solution, such as an aqueous sodium bicarbonate solution, followed by extraction of the substituted, fused, polycyclic nitrogen-containing aromatic compounds with an organic solvent.

The alcohol group of the compounds represented by Structural Formulas (II), (IV), (VI), (VIII) and (IX) can be further converted into other useful functionalities by reacting the alcohol with an activating agent which converts the alcohol into a suitable leaving group. Suitable activating agents include thionyl halides, sulfonyl halides, $POCl_3$, $PCl_5$, and $PCl_3$. For example, the alcohol can be converted to a halide by reacting it with thionyl halide. Alternatively, the alcohol can be converted to a sulfonate ester, such as a mesylate, by reacting it with a sulfonyl chloride, such as methanesulfonyl chloride. The leaving group can then be displaced by a suitable nucleophilic compound. Examples of nucleophilic compounds include amines, $RO^-$ and $RS^-$. R is an alkyl group, a substituted alcohol group, an aryl group and a substituted aryl group. Amines are preferred nucleophilic compounds. Pyrrolidine is a particularly preferred nucleophilic compound.

The term "aliphatic groups," as used herein, include straight chained, branched C1–C20 hydrocarbons or cyclic C3–C20 hydrocarbons which are completely saturated or which contain one or more units of unsaturation. In one example, the aliphatic group is a C1–C10 alkyl group.

Aryl groups include carbocyclic aromatic groups such as phenyl, naphthyl, and anthracyl, and heteroaryl groups such as thienyl, furanyl, thiazolyl and oxazolyl. Aryl groups also include fused polycyclic aromatic ring systems in which a carbocyclic aromatic ring or heteroaryl ring is fused to one or more other heteroaryl rings. Examples include benzothienyl, benzofuranyl, benzothiazolyl and benzooxazolyl.

Suitable substituents for a 2,3-dihydrofuran and for an aryl group, aliphatic group, and the 2-hydroxy-1-ethyl group in Structural Formulas (II)–(IX) are those which are compatible with the reaction, i.e., do not significantly reduce the yield of the reaction and do not cause a significant amount of side reactions. A 2,3-dihydrofuran, an aryl group, an aliphatic group, and a 2-hydroxy-1-ethyl group can have more than one substituent. Suitable substituents generally include groups which are not strongly basic and or highly electrophilic. Examples of suitable substituents include aliphatic groups, a substituted aliphatic group, aryl groups, a substituted aryl, halogens, halogenated alkyl groups (e.g., trihalomethyl), nitro, nitrile, —C(O)NHR, —C(O)NRR, —NHC(O)R, —NRC(O)R, —OR, —SR, —S(O)R, or —S(O)₂R, wherein each R is independently an aliphatic group, a substituted aliphatic group, an aryl group or a substituted aryl group. Alipatic and aryl substituents can be further substituted at one or more positions with an aliphatic group, an aryl group, a halogen, a halogenated alkyl group (e.g., trihalomethyl), nitro, nitrile, —C(O)NHR, —C(O)NRR, —NHC(O)R, —NRC(O)R, —OR, —SR, —S(O)R, or —S(O)₂R.

Although strongly basic groups such as amines and highly electrophilic groups such as acid chlorides, ketones, aldehydes and esters are not generally compatible with the reaction used in the method of the present invention, these functional groups can be present if they are first converted to a suitable protected form. For example, an aldehyde or a ketone can be protected by forming an acetal or a ketal, respectively, and an amine group can be protected by forming an amide. The protecting group can then be removed after the reaction. Protecting groups are well known in the art and are described in, for example, Greene and Wuts, "Protective Groups in Organic Synthesis", John Wiley & Sons (1991), the entire teachings of which are incorporated into this application by reference. The skilled artisan can select, using no more than routine experimentation, suitable protecting groups for use in the disclosed synthesis as well as conditions for applying and removing the protecting groups.

Salts derived from an aryl hydrazine represented by Structural Formulas (III) and (VII) are prepared by reacting the aryl hydrazine with a mineral acid. Examples of suitable salts include the hydrochloride salt, the hydrobromide salt, the hydroiodide salt, the salts of H₂SO₄, HNO₃, H₃PO₄ and the like.

The invention is illustrated by the following examples which are not intended to be limiting in any way.

EXAMPLES

Example 1

Figure 2:
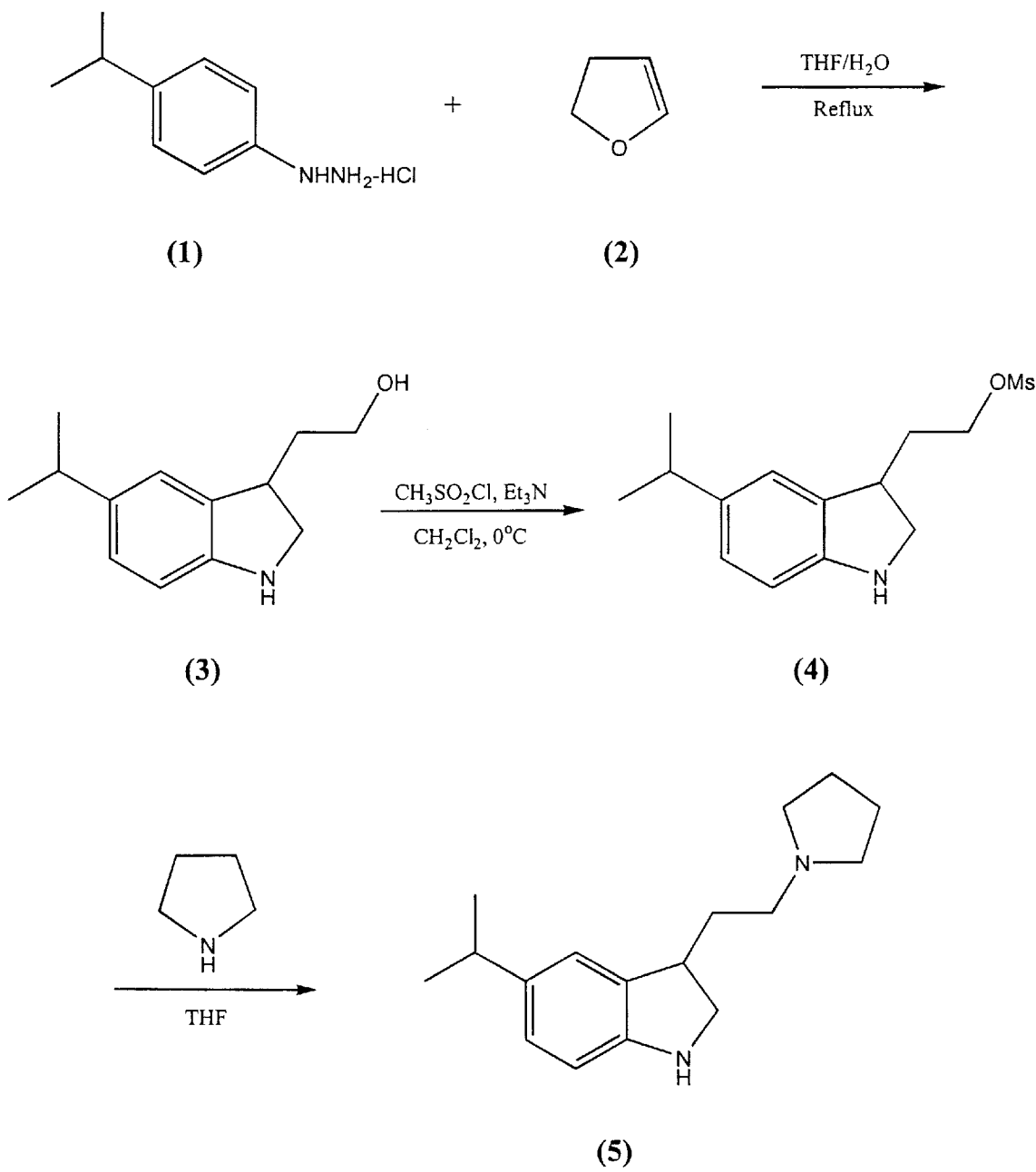
FIG. 2 is a reaction scheme showing the conversion of 4-isopropylphenylhydrazine and 2,3-dihydrofuran to 5-isopropyl-3-[2(N-pyrrolidino)ethyl]-1 H-indole.

Preparation of 5-Isopropyltryptophol (FIG. 2, Compound (3)):

A solution of 2,3-dihydrofuran (540 mL) in THF (1.2 L) was added slowly to a solution of 4-isopropylphenylhydrazine hydrochloride (1.2 kg, 6.43 mol) in 9.6 L of THF and 600 mL of H₂O through an addition funnel at room temperature. At the end of the addition a solid was formed and temperature reached 60° C. The reaction mixture was refluxed for 5 hours and monitored by TLC and HPLC. After cooling, solvent was removed under reduced pressure. The residue was treated with H₂O and extracted with EtOAc (2×7 L). The organic layers were combined, washed with water (3 L), dried over anhydrous sodium sulfate and evaporated to give a residual dark brown material which was purified by silica-gel flash column chromatography and elution with 30% EtOAc/Hexane to give 570 g (45%) of 90% pure product.

Example 2

Preparation of 5-Isopropyl-3-[2(N-pyrrolidino)ethyl]-1 H-indole (FIG. 2, Compound (5)):

Methanesulfonyl chloride (60.9 g., 532 mmol) was added slowly to a mixture of 5-isopropyltryptophol (90.0 g, 443 mmol) and triethylamine (67.2 g, 665 mmol) in methylene chloride (1500 mL) at 0° C. The reaction mixture was stirred for 1.5 hours. Reaction progress was checked by TLC (silica-gel, 50% EtOAc/Hexane) which showed that the starting material was consumed. The mixture was washed with H₂O and saturated NaHCO₃ to remove excess methanesulfonyl chloride. The organic layer was concentrated under reduced pressure. The residue was dissolved in THF (350 mL) and added very slowly through an addition funnel to a refluxing solution of pyrrolidine (127.8, 1797 mmol) in THF (1650 mL) at 65° C. After the addition was completed, the reaction was allowed to stir at this temperature for 16 hours. The reaction was cooled to room temperature, then concentrated under reduced pressure to dryness. The residue was treated with H₂O and extracted with EtOAc (2×1 L). The organic layers were combined, dried over Na₂SO₄ and concentrated to dryness to afford a crude product 111 g (98%).

Example 3

Crystallization of the 5-Isopropyl-3-[2(N-pyrrolidino)ethyl)]-1-H-indole Succinic Acid Salt The crude material from Example 2 (111 g, 432 mmol) was dissolved in hot methanol (600 mL) and added to a hot solution of succinic acid (51.1 g, 432 mmol) in MeOH (250 mL). After stirring for 5 hours, the white solid formed was filtered washed with ethanol to yield 111 g (70%) of 98% pure product.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of preparing a fused polycyclic nitrogen-containing heteroaromatic compound represented by the following structural formula:

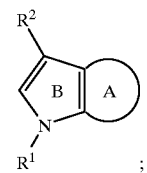

or a physiologically acceptable salt thereof, wherein:

R¹ is —H, an aliphatic group, a substituted aliphatic group, an aryl group or a substituted aryl group;

R² is a substituted or unsubstituted 2-hydroxy-1-ethyl group;

ring A is a substituted or unsubstituted aryl group; and ring B is substituted or unsubstituted at position two;

said method comprising the step of reacting a substituted or unsubstituted 2,3-dihydrofuran with a salt of an aryl hydrazine, wherein the aryl hydrazine is represented by the structural formula:

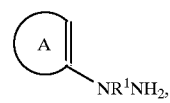

thereby forming said fused polycyclic nitrogen-containing heteroaromatic compound.

2. The method of claim 1 further comprising the steps of:

a) reacting the fused polycyclic nitrogen-containing compound with an activating agent, thereby forming a first intermediate; and b) reacting the first intermediate with a nucleophilic compound.

3. The method of claim 2, wherein the activating agent is a thionyl halide or a sulfonyl chloride.

4. The method of claim 3, wherein the activating agent is methanesulfonyl chloride.

5. The method of claim 4, wherein the nucleophilic compound is an amine.

6. The method of claim 5, wherein the amine is pyrrolidine.

7. The method of claim 1, wherein the 2,3-dihydrofuran is unsubstituted and wherein the fused polycyclic nitrogen-containing heteroaromatic compound is represented by the following structural formula:

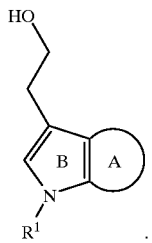

8. The method of claim 1, wherein the aryl hydrazine is a substituted or unsubstituted phenyl hydrazine and, wherein the fused polycyclic nitrogen-containing heteroaromatic compound is represented by the following structural formula:

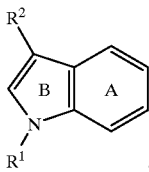

9. The method of claim 8, wherein the 2,3-dihydrofuran is unsubstituted and, wherein the fused polycyclic nitrogen-containing heteroaromatic compound is represented by the following structural formula:

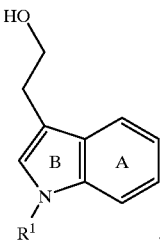

10. The method of claim 9, wherein $R^1$ is —H.

11. The method of claim 9, wherein $R^1$ is —CH$_3$.

12. A method of preparing a fused polycyclic nitrogen-containing heteroaromatic compound represented by the following structural formula:

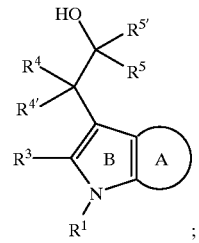

or a physiologically acceptable salt thereof, wherein:

$R^1$ is —H, an aliphatic group, a substituted aliphatic group, an aryl group or a substituted aryl group;

$R^3$, $R^4$, $R^{4'}$, $R^5$, and $R^{5'}$ are each, independently, —H, a aliphatic group, a substituted aliphatic group, an aryl group, a substituted aryl group, a halogen, a halogenated aliphatic group, nitro, nitrile, —C(O)NHR, —C(O)NRR, —NHC(O)R, —NRC(O)R, —OR, —SR, —S(O)R, or —S(O)$_2$R;

R is an aliphatic group, a substituted aliphatic group, an aryl group or a substituted aryl group; and ring A is a substituted or unsubstituted aryl group;

said method comprising the step of reacting a salt derived from a substituted or unsubstituted aryl hydrazine represented by the following structural formula:

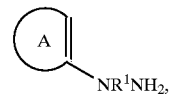

with a compound represented by the following structural formula:

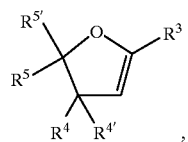

thereby forming said fused polycyclic nitrogen-containing heteroaromatic compound.

* * * * *